US012773184B2

(12) United States Patent
Katagiri et al.

(10) Patent No.: US 12,773,184 B2
(45) Date of Patent: Oct. 27, 2026

(54) CART FOR PORTABLE ULTRASOUND DIAGNOSTIC APPARATUS AND PORTABLE ULTRASOUND DIAGNOSTIC UNIT HAVING SEAT, HANDLES ON BOTH SIDES AND COLUMNAR SUPPORT

(71) Applicant: FUJIFILM Corporation, Tokyo (JP)

(72) Inventors: Kengo Katagiri, Tokyo (JP); Takayoshi Saito, Tokyo (JP); Ryosuke Ogura, Tokyo (JP); Takuro Iwaki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 52 days.

(21) Appl. No.: 19/075,765

(22) Filed: Mar. 10, 2025

(65) Prior Publication Data

US 2025/0295384 A1 Sep. 25, 2025

(30) Foreign Application Priority Data

Mar. 19, 2024 (JP) ................................ 2024-043108

(51) Int. Cl.
*A61B 8/00* (2006.01)

(52) U.S. Cl.
CPC .......... *A61B 8/4405* (2013.01); *A61B 8/4427* (2013.01)

(58) Field of Classification Search
CPC ... A61B 8/4405; A61B 8/4427; A61B 8/4411; A61B 8/4433
See application file for complete search history.

(56) References Cited

U.S. PATENT DOCUMENTS

| | | | | |
|---|---|---|---|---|
| 2003/0220564 A1 | 11/2003 | Wilkins et al. | | |
| 2009/0326380 A1 | 12/2009 | Shin et al. | | |
| 2010/0056913 A1 | 3/2010 | Hirakui et al. | | |
| 2013/0300075 A1* | 11/2013 | Arceta | ................ | A61G 12/001 280/33.991 |

(Continued)

FOREIGN PATENT DOCUMENTS

| | | |
|---|---|---|
| JP | 2007-006968 A | 1/2007 |
| JP | 2010-005400 A | 1/2010 |
| JP | 2017-000421 A | 1/2017 |

OTHER PUBLICATIONS

The extended European search report issued by the European Patent Office on Jul. 28, 2025, which corresponds to European Patent Application No. 25163061.2-1122 and is related to U.S. Appl. No. 19/075,765.

*Primary Examiner* — Serkan Akar
(74) *Attorney, Agent, or Firm* — Studebaker Brackett PLLC

(57) ABSTRACT

An ultrasound diagnostic unit includes a portable ultrasound diagnostic apparatus, a seat on which the portable ultrasound diagnostic apparatus is placed, handles that are connected to the seat, a columnar support that supports the seat, a plurality of leg portions that support the columnar support, and casters disposed at the leg portions. The handles include a front handle disposed in front of the seat, side handles disposed on right and left sides with respect to the seat, and a rear handle disposed behind the seat. The handles are connected to each other to surround the seat. Each of the two side handles includes a front portion that is connected to the front handle and that is inclined rearward and downward and a body portion that extends rearward from a rear end of the front portion.

12 Claims, 14 Drawing Sheets

(56) References Cited

U.S. PATENT DOCUMENTS

| | | | | |
|---|---|---|---|---|
| 2014/0117635 | A1 | 5/2014 | Ninomiya et al. | |
| 2015/0105660 | A1* | 4/2015 | Ninomiya ............ | A61B 8/4427 600/437 |
| 2017/0027541 | A1* | 2/2017 | Henderson ........... | A61B 8/4405 |
| 2018/0098751 | A1* | 4/2018 | Messina ............... | A61B 8/4405 |
| 2019/0365352 | A1 | 12/2019 | Song et al. | |
| 2020/0060649 | A1* | 2/2020 | Nally ................... | A61B 8/4433 |

* cited by examiner

CART FOR PORTABLE ULTRASOUND DIAGNOSTIC APPARATUS AND PORTABLE ULTRASOUND DIAGNOSTIC UNIT HAVING SEAT, HANDLES ON BOTH SIDES AND COLUMNAR SUPPORT

CROSS-REFERENCE TO RELATED APPLICATIONS

This application claims benefit of priority to Japanese Patent Application No. 2024-043108 filed Mar. 19, 2024, the entire contents of which are incorporated herein by reference.

BACKGROUND OF THE INVENTION

1. Field of the Invention

The present disclosure relates to a cart for an ultrasound diagnostic apparatus and an ultrasound diagnostic unit, and particularly to a technology regarding a cart handle.

2. Description of the Related Art

In ultrasound examination of a living body, an ultrasound diagnostic apparatus is used. The ultrasound diagnostic apparatus is a medical apparatus that generates and displays an ultrasound image based on a received signal that is obtained through transmission and reception of ultrasound waves. A tomographic image is known as a representative ultrasound image.

Portable ultrasound diagnostic apparatuses are being used. Examples of such portable ultrasound diagnostic apparatuses include a laptop type ultrasound diagnostic apparatus, which can be carried in a user's hand. In addition, the portable ultrasound diagnostic apparatuses are often used after being placed on a cart. A laptop type portable ultrasound diagnostic apparatus is moved to a position right beside a subject after being placed on a cart and the portable ultrasound diagnostic apparatus is opened and operated in a state where the portable ultrasound diagnostic apparatus is placed on the cart such that a probe is extended up to a subject and ultrasound waves are transmitted and received to and from the subject.

Disclosed in JP2010-5400A is a portable ultrasound diagnostic machine that includes a body portion, a curved handle portion bonded to the body portion and a display portion bonded to the handle portion. Disclosed in JP2017-421A is, in relation to an ultrasound diagnostic system, a configuration in which a columnar support for a carriage is provided with an intermediate seat on which a tablet computer serving as an auxiliary input device can be placed.

SUMMARY OF THE INVENTION

An ultrasound diagnostic unit includes a cart and a portable ultrasound diagnostic apparatus placed on the cart. A user transports the ultrasound diagnostic unit, performs fine adjustment of the position of the ultrasound diagnostic unit, or revolves the ultrasound diagnostic unit. Therefore, a cart handle with which it is easy to realize such movements of the ultrasound diagnostic unit is desired.

In addition, a side portion of the portable ultrasound diagnostic apparatus is provided with a connector portion (a port) to which a connector of a probe is connected and an air discharge portion through which air that has cooled the inside of the apparatus is discharged. Therefore, the side portion of the portable ultrasound diagnostic apparatus needs to be made open.

An object of the present disclosure is to provide an ultrasound diagnostic unit with which a side portion of a portable ultrasound diagnostic apparatus can be made open and which is moved easily. Alternatively, an object of the present disclosure is to provide a cart for an ultrasound diagnostic apparatus which is a part of the ultrasound diagnostic unit.

According to an aspect of the present disclosure, there is provided an ultrasound diagnostic unit comprising a portable ultrasound diagnostic apparatus, a seat on which the portable ultrasound diagnostic apparatus is placed, handles that are connected to the seat, a columnar support that supports the seat, a plurality of leg portions that support the columnar support, and casters that are disposed at the leg portions. The handles include a front handle disposed in front of the seat, side handles disposed on right and left sides with respect to the seat, and a rear handle disposed behind the seat, the handles are connected to each other to surround the seat, and each of two side handles includes a front portion that is connected to the front handle and that is inclined rearward and downward and a body portion that extends rearward from a rear end of the front portion.

According to an aspect of the present disclosure, there is provided a cart for an ultrasound diagnostic apparatus, the cart comprising a seat on which a portable ultrasound diagnostic apparatus is placed, handles that are connected to the seat, a columnar support that supports the seat, a plurality of leg portions that support the columnar support, and casters that are disposed at the leg portions. The handles include a front handle disposed in front of the seat, side handles disposed on right and left sides with respect to the seat, and a rear handle disposed behind the seat, the handles are connected to each other to surround the seat, and each of two side handles includes a front portion that is connected to the front handle and that is inclined rearward and downward and a body portion that extends rearward from a rear end of the front portion.

According to the present disclosure, it is possible to easily move an ultrasound diagnostic unit or a cart for an ultrasound diagnostic apparatus. In addition, side portions of a portable ultrasound diagnostic apparatus can be made open.

DESCRIPTION OF THE PREFERRED EMBODIMENTS

Figure 1:
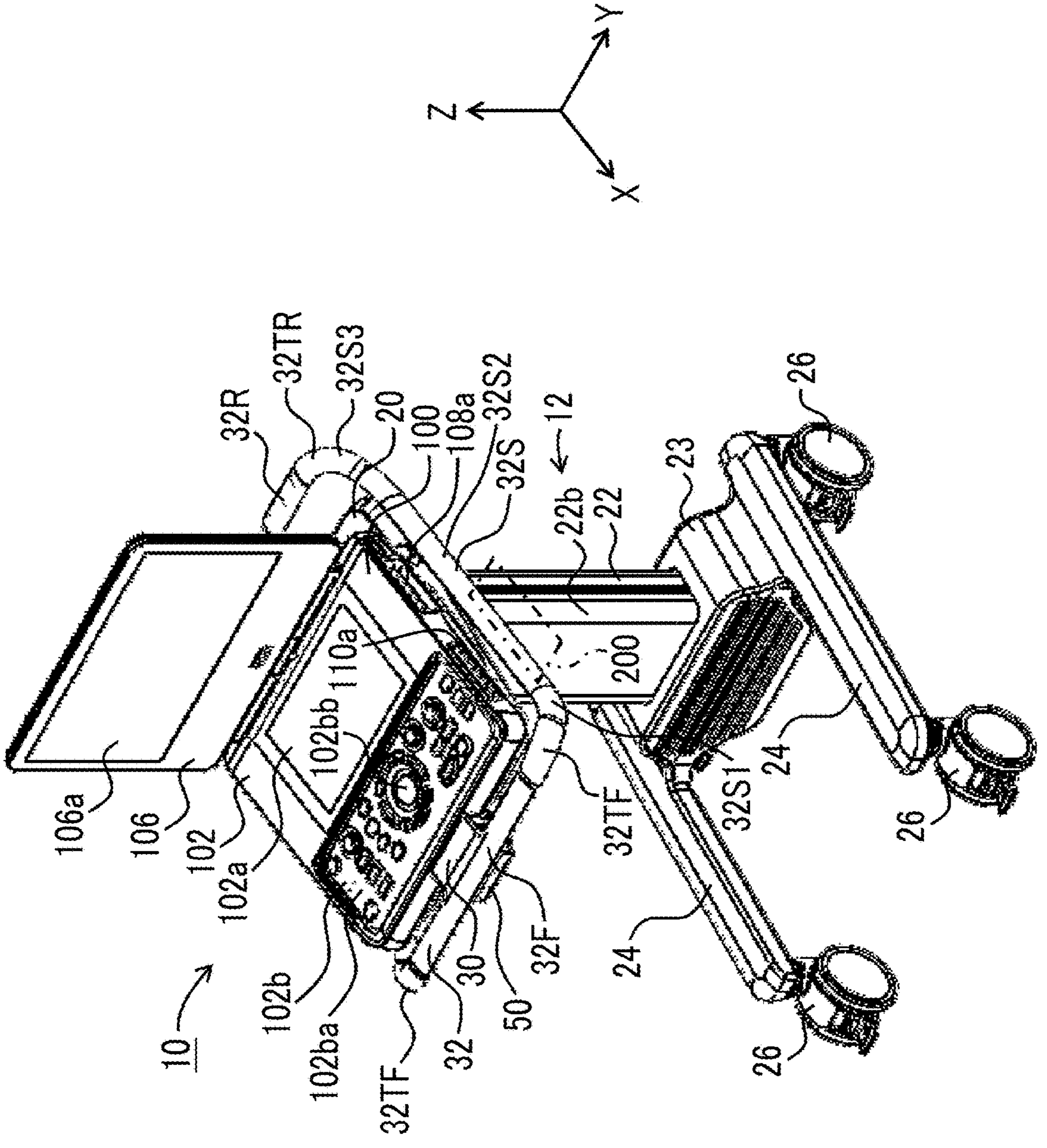
FIG. 1 is a perspective view showing a front surface and a right side surface of an ultrasound diagnostic unit.

Hereinafter, an embodiment will be described with reference to the drawings. The present disclosure is not limited to the embodiment described herein. In all of the drawings, the same elements are denoted by the same reference numerals and the description thereof will not be repeated. In this specification, unless otherwise specified, directions represented by arrows X, Y, and Z in FIG. 1 will be referred to as "a forward direction", "a rightward direction", and "an upward direction", and directions opposite thereto will be referred to as "a rearward direction", "a leftward direction", and "a downward direction". A direction along the arrow Z coincides with a direction in which the gravity acts, that is, a vertical direction.

(1) Outline of Embodiment

An ultrasound diagnostic unit according to an embodiment comprises a portable ultrasound diagnostic apparatus, a seat on which the portable ultrasound diagnostic apparatus is placed, handles that are connected to the seat, a columnar support that supports the seat, a plurality of leg portions that support the columnar support, and casters that are disposed at the leg portions. The handles include a front handle disposed in front of the seat, side handles disposed on right and left sides with respect to the seat, and a rear handle disposed behind the seat. The handles are connected to each other to surround the seat. Each of two side handles includes a front portion that is connected to the front handle and that is inclined rearward and downward and a body portion that extends rearward from a rear end of the front portion.

According to a configuration as described above, since the handles are provided around the seat, a user can access the handles and move the ultrasound diagnostic unit regardless of the user's position with respect to the ultrasound diagnostic unit. For example, the user can finely adjust the position of the ultrasound diagnostic unit or can revolve the ultrasound diagnostic unit while gripping the front handle or the rear handle with one hand and gripping the side handle with the other hand. In addition, since the two side handles are provided at relatively low positions, side portions of the portable ultrasound diagnostic apparatus can be made open. Therefore, it is easy to access a connector (a port) or the like of a side portion of the portable ultrasound diagnostic apparatus.

In the embodiment, the seat includes a palm rest that is disposed in front of an operation portion of the portable ultrasound diagnostic apparatus while being at a center in a lateral direction. The palm rest is positioned between the front handle and the operation portion of the portable ultrasound diagnostic apparatus. The front handle, the palm rest, and the operation portion of the portable ultrasound diagnostic apparatus form a continuous upper surface. According to such a configuration, a user (for example, an operator) can operate the portable ultrasound diagnostic apparatus with a wrist placed on the front handle and the palm rest.

In the embodiment, the rear handle is provided at a position higher than the front handle. According to such a configuration, in a case where the front handle is at a relatively low position in consideration of a case where a user (for example, an operator) operates the portable ultrasound diagnostic apparatus in a seated position, the rear handle is at a high position. Accordingly, in a case where a user (for example, an operator) transports the ultrasound diagnostic unit while holding the rear handle, the user can easily perform the transportation.

In the embodiment, the body portion of each of the two side handles is inclined upward in a direction from a front side to a rear side. According to such a configuration, for example, in a case where a probe holder, a holder that holds a jelly container, a holder that holds a tray, or the like is attached to the body portion of the side handle, an object held by the holder faces a diagonally front side. Therefore, a user (for example, an operator) can easily access the object held by the holder.

In the embodiment, a cross-sectional outer shape of the handles is a flat oval shape. The front handle and the rear handle are disposed such that flat surfaces of the front handle and the rear handle face a vertical direction. The two side handles are disposed such that flat surfaces of the side handles face a lateral direction. According to such a configuration, a user can move the ultrasound diagnostic unit while holding the front handle or the rear handle with a hand being in close contact with an upper flat surface of the handle. In addition, since the flat surfaces of the two side handles face the lateral direction, protrusion of the side handles in the lateral direction can be suppressed.

In the embodiment, a center portion of the rear handle in a lateral direction is cut out such that the rear handle is divided in the lateral direction. The rear handle consists of a rear handle element on the left side and a rear handle element on the right side. The seat includes an operation portion (will be referred to as a binding operation portion) used to bind the portable ultrasound diagnostic apparatus to the seat, the operation portion being provided at a rear surface that faces at least one of a gap region between the two rear handle elements or a region below the gap region. According to such a configuration, since the gap region is present between the two rear handle elements, a user can easily access the binding operation portion through the gap region.

In the embodiment, the columnar support supports the seat to be raisable and lowerable. The ultrasound diagnostic unit further includes a push-button used to raise or lower the seat. The push-button is disposed below a center of the front handle in the lateral direction. The seat locked to be unraisable and unlowerable is unlocked in a case where the push-button is pressed. Note that the expression "being locked to be unraisable and unlowerable" means a state where the seat is restricted from being raised and lowered and is locked such that the seat cannot be raised and lowered. The expression "the seat locked to be unraisable and unlowerable is unlocked" means that the seat is made raisable and lowerable.

According to a configuration as described above, a user (for example, an operator) can unlock the seat locked to be unraisable and unlowerable by pressing the push-button with a thumb in a state where a hand is placed on a left portion or a right portion of the front handle. In addition, the user also can unlock the seat locked to be unraisable and unlowerable by pressing the push-button with the thumbs of both hands in a state where both hands placed on the right and left portions of the front handle.

A cart for an ultrasound diagnostic apparatus according to an embodiment comprises a seat on which a portable ultrasound diagnostic apparatus is placed, handles that are connected to the seat, a columnar support that supports the seat, a plurality of leg portions that support the columnar support, and casters that are disposed at the leg portions. The handles include a front handle disposed in front of the seat, side handles disposed on right and left sides with respect to the seat, and a rear handle disposed behind the seat. The handles are connected to each other to surround the seat. Each of two side handles includes a front portion that is connected to the front handle and that is inclined rearward and downward and a body portion that extends rearward from a rear end of the front portion.

According to a configuration as described above, since the handles are provided around the seat, a user can access the handles and move the cart regardless of the user's position with respect to the cart. In addition, since the two side handles are provided at relatively low positions, side portions of the portable ultrasound diagnostic apparatus can be made open in a case where the portable ultrasound diagnostic apparatus is placed on the seat of the cart. Therefore, it is easy to access a connector (a port) or the like of a side portion of the portable ultrasound diagnostic apparatus.

In the cart for an ultrasound diagnostic apparatus according to the embodiment, the rear handle is provided at a position higher than the front handle. According to such a configuration, in a case where the front handle is at a relatively low position in consideration of a case where a user (for example, an operator) operates the portable ultrasound diagnostic apparatus in a seated position, the rear handle is at a high position. Accordingly, in a case where a user (for example, an operator) transports the cart while holding the rear handle, the user can easily perform the transportation.

(2) Details of Embodiment

Figure 2:
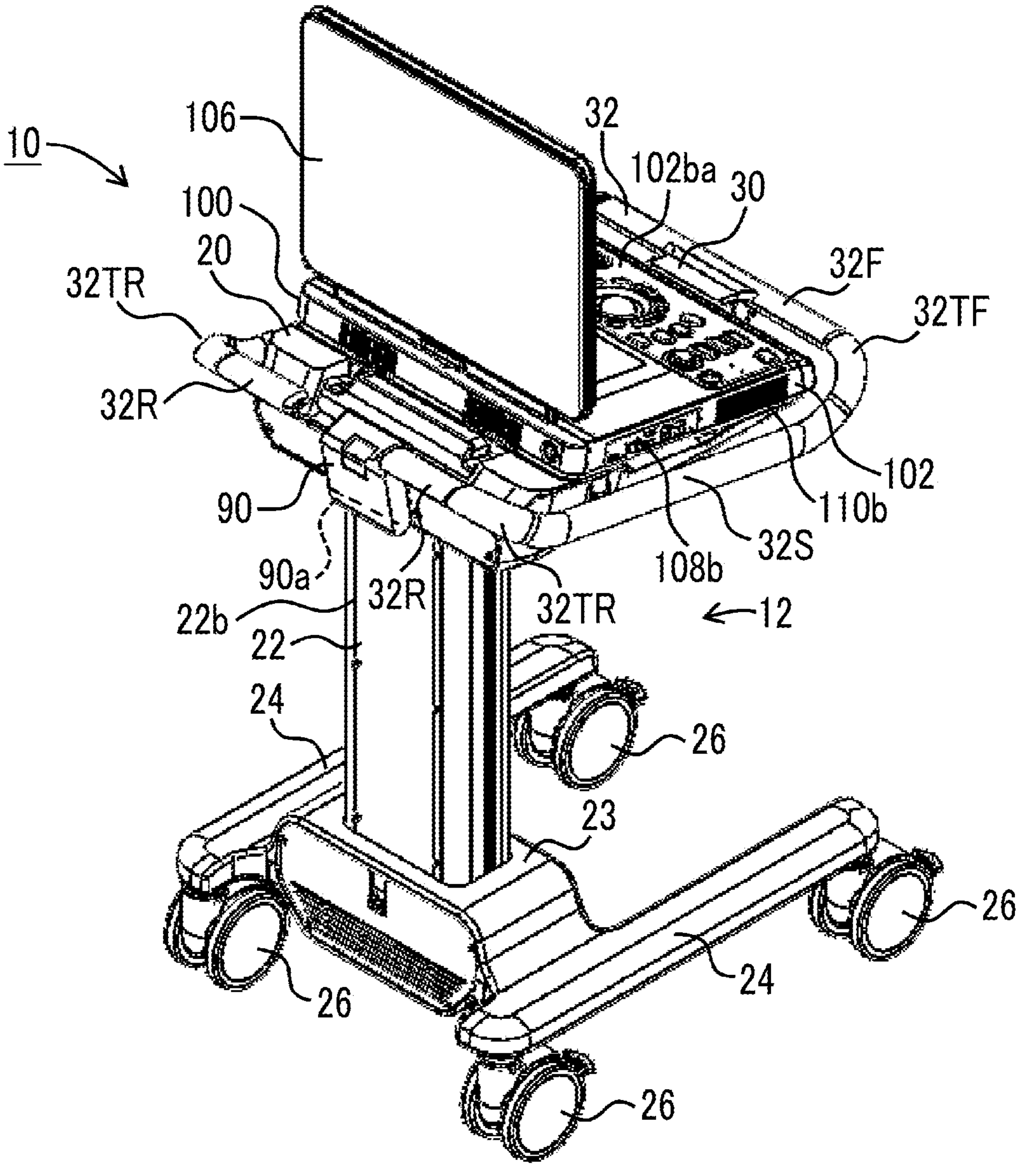
FIG. 2 is a perspective view showing a rear surface and a left side surface of the ultrasound diagnostic unit.
Figure 3:
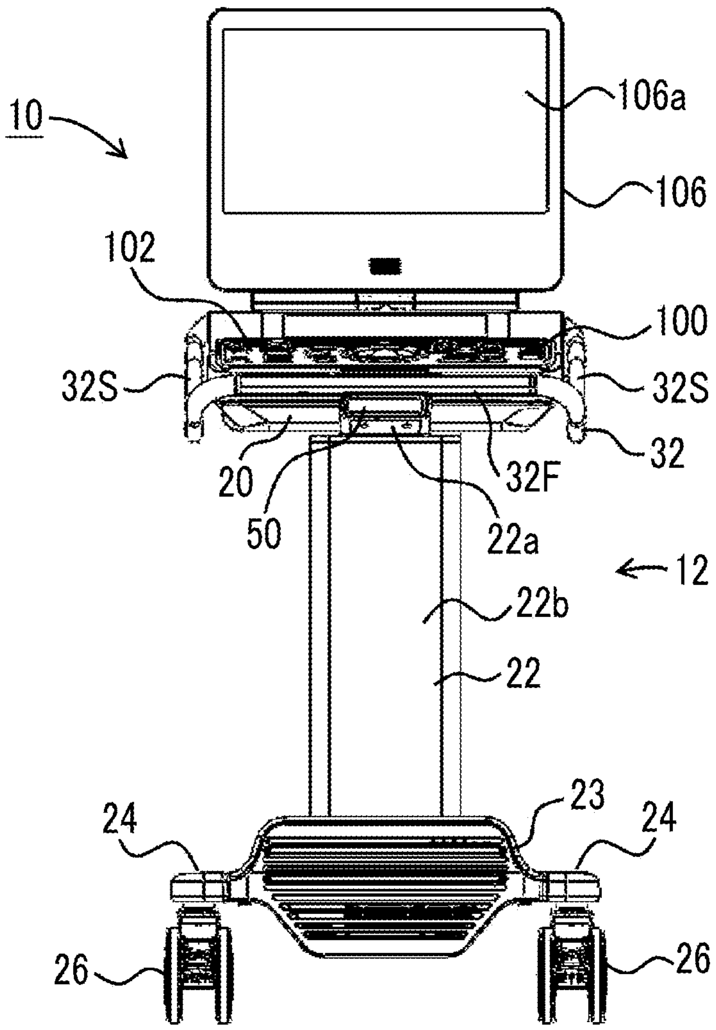
FIG. 3 is a front view of the ultrasound diagnostic unit.
Figure 4:
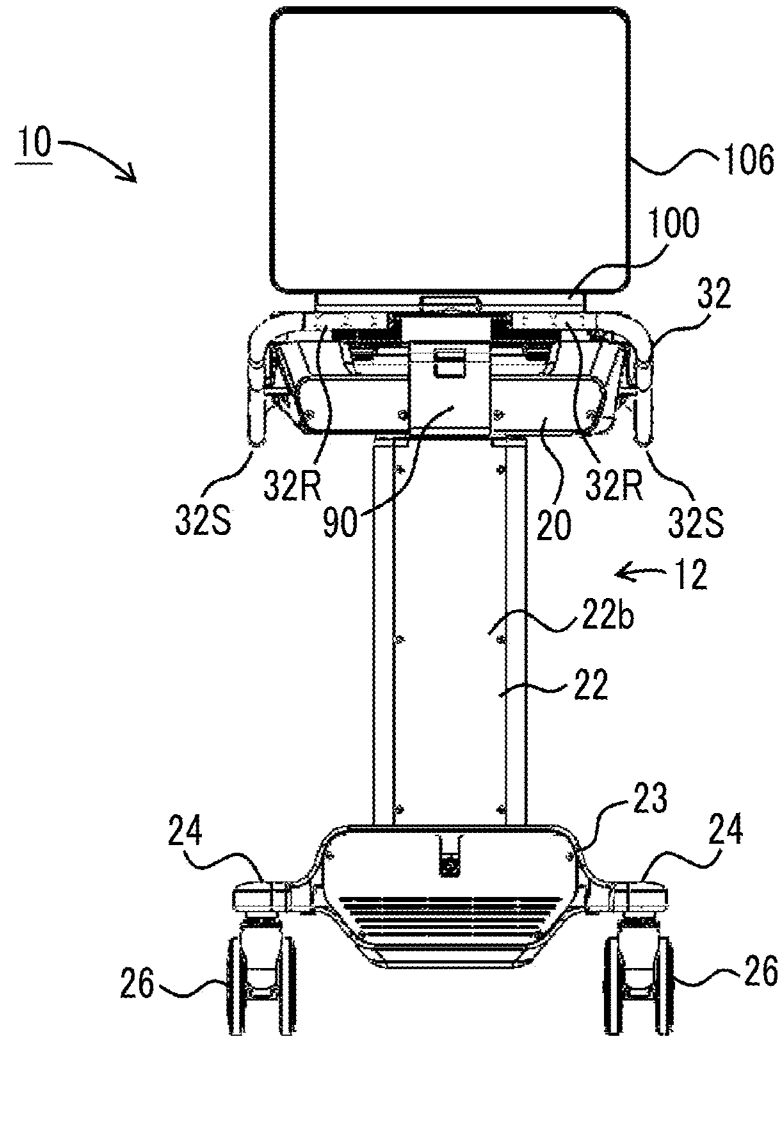
FIG. 4 is a rear view of the ultrasound diagnostic unit.
Figure 5:
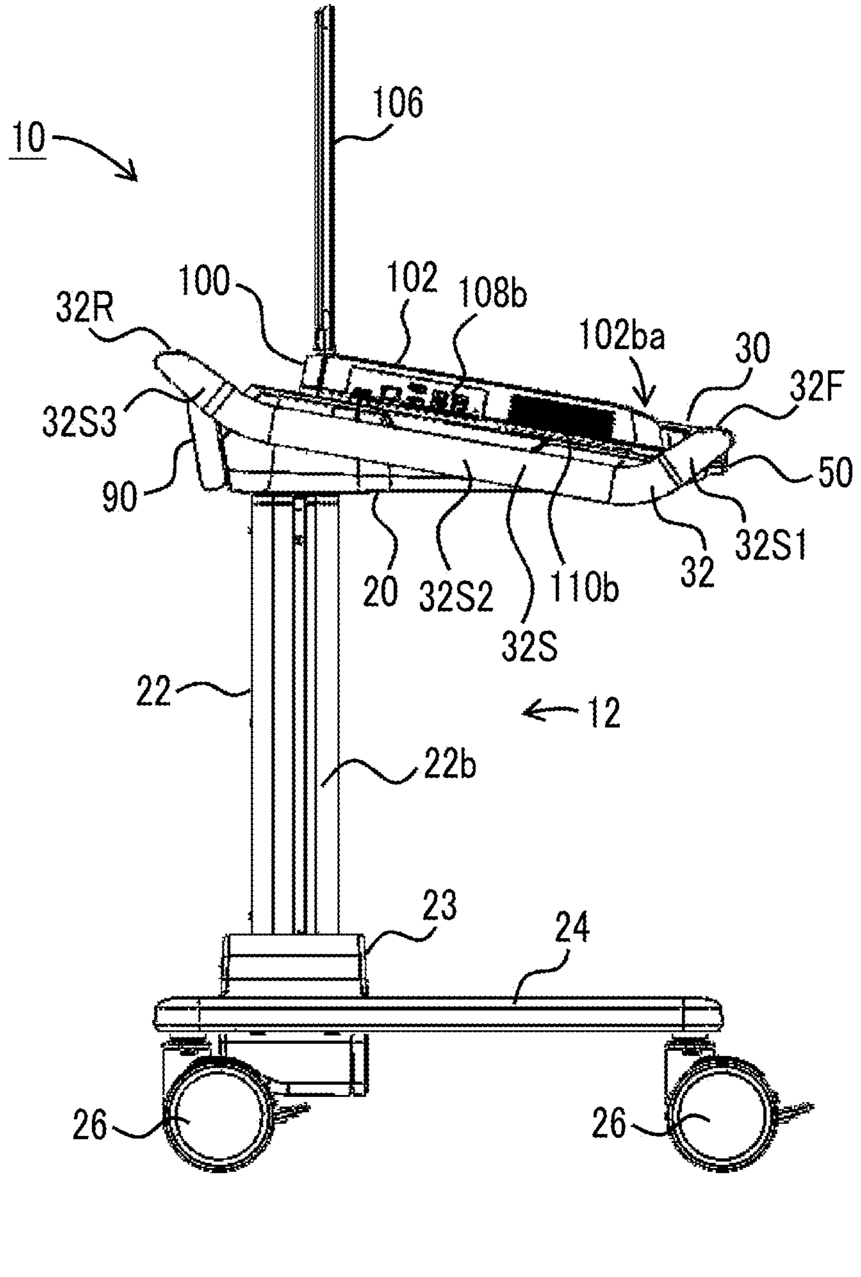
FIG. 5 is a left-side view of the ultrasound diagnostic unit.
Figure 6:
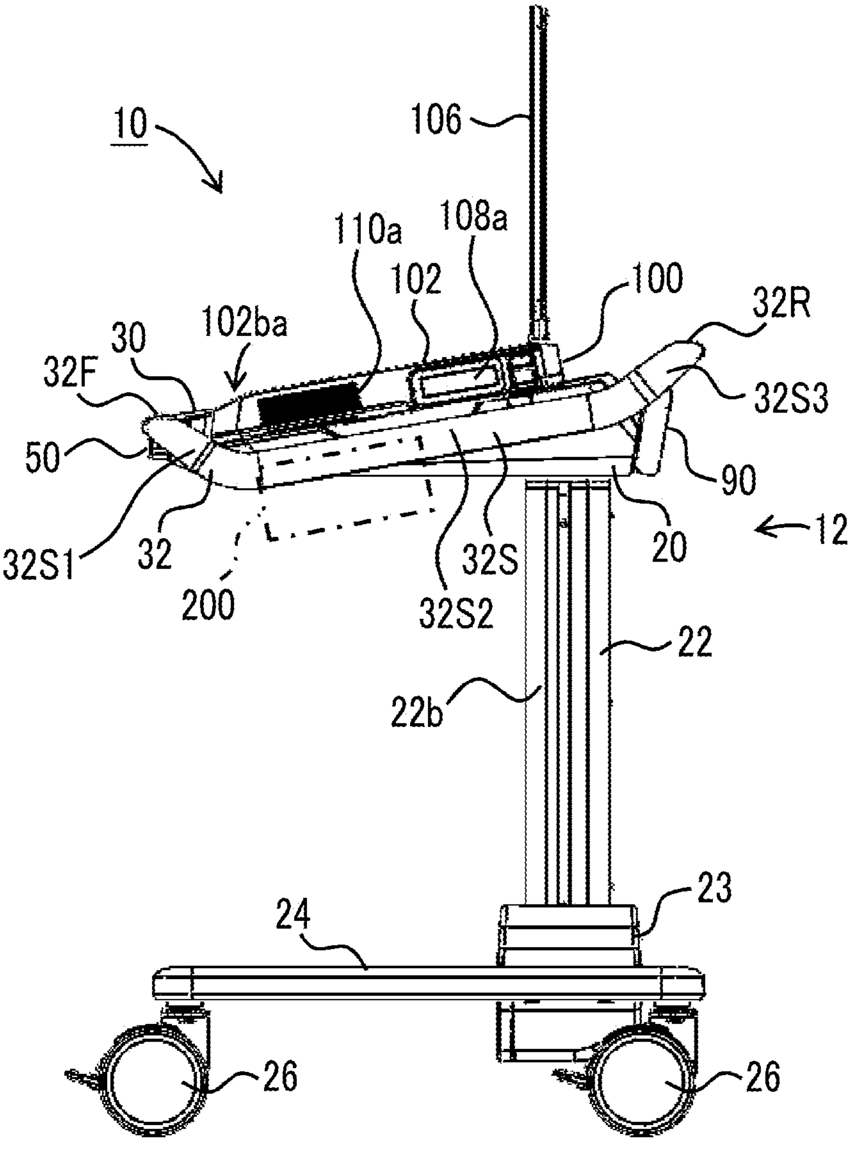
FIG. 6 is a right-side view of the ultrasound diagnostic unit.
Figure 7:
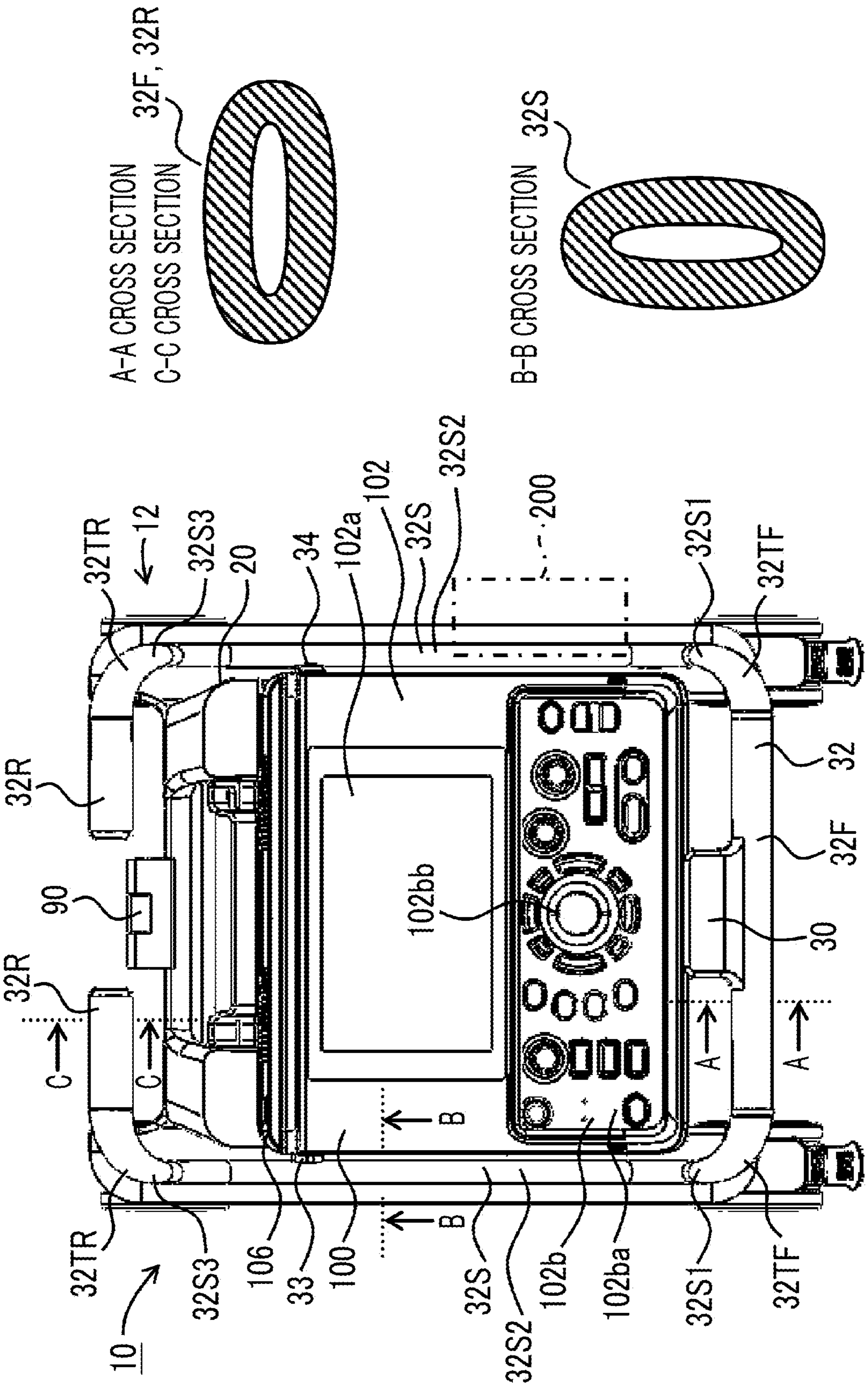
FIG. 7 is a plan view of the ultrasound diagnostic unit.

FIG. 1 shows an ultrasound diagnostic unit 10 according to the embodiment. The ultrasound diagnostic unit 10 is installed in a medical institution such as a hospital and is used for ultrasound examination for a subject. FIG. 1 is a perspective view showing a front surface and a right side surface of the ultrasound diagnostic unit 10. FIG. 2 is a perspective view showing a rear surface and a left side surface of the ultrasound diagnostic unit 10. FIG. 3 is a front view of the ultrasound diagnostic unit 10. FIG. 4 is a rear view of the ultrasound diagnostic unit 10. FIG. 5 is a left-side view of the ultrasound diagnostic unit 10. FIG. 6 is a right-side view of the ultrasound diagnostic unit 10. FIG. 7 is a plan view of the ultrasound diagnostic unit 10.

Figure 13:
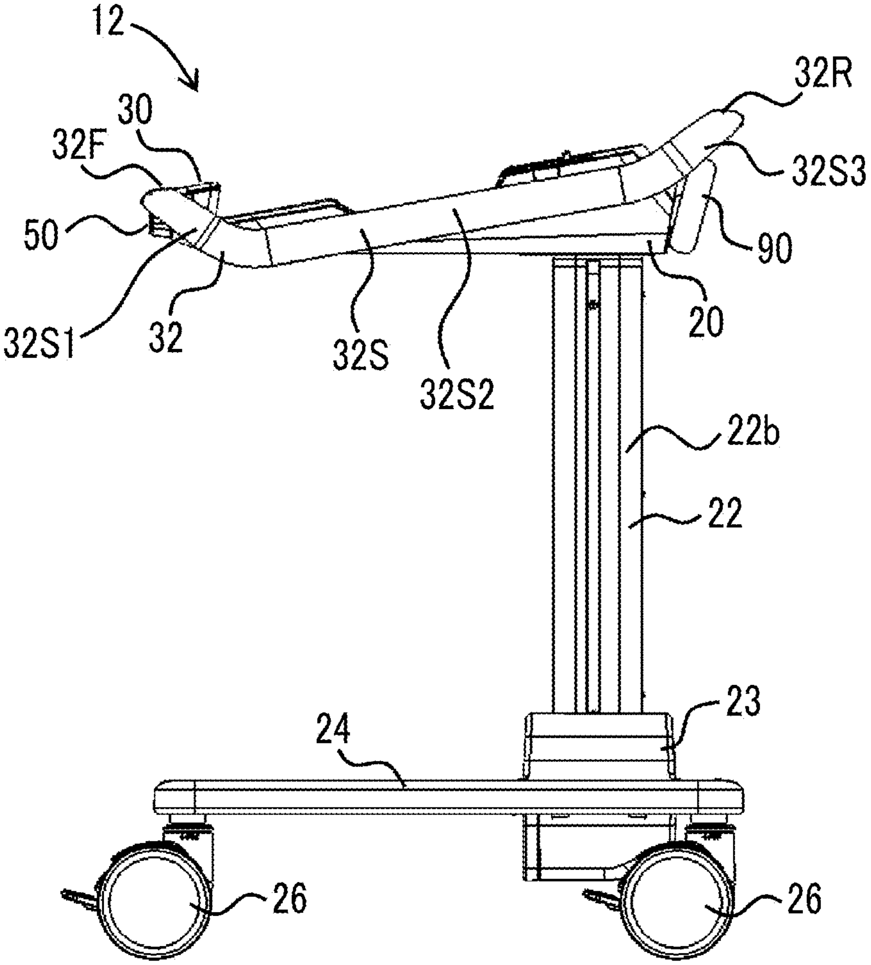
FIG. 13 is a right-side view of a cart for an ultrasound diagnostic apparatus.
Figure 14:
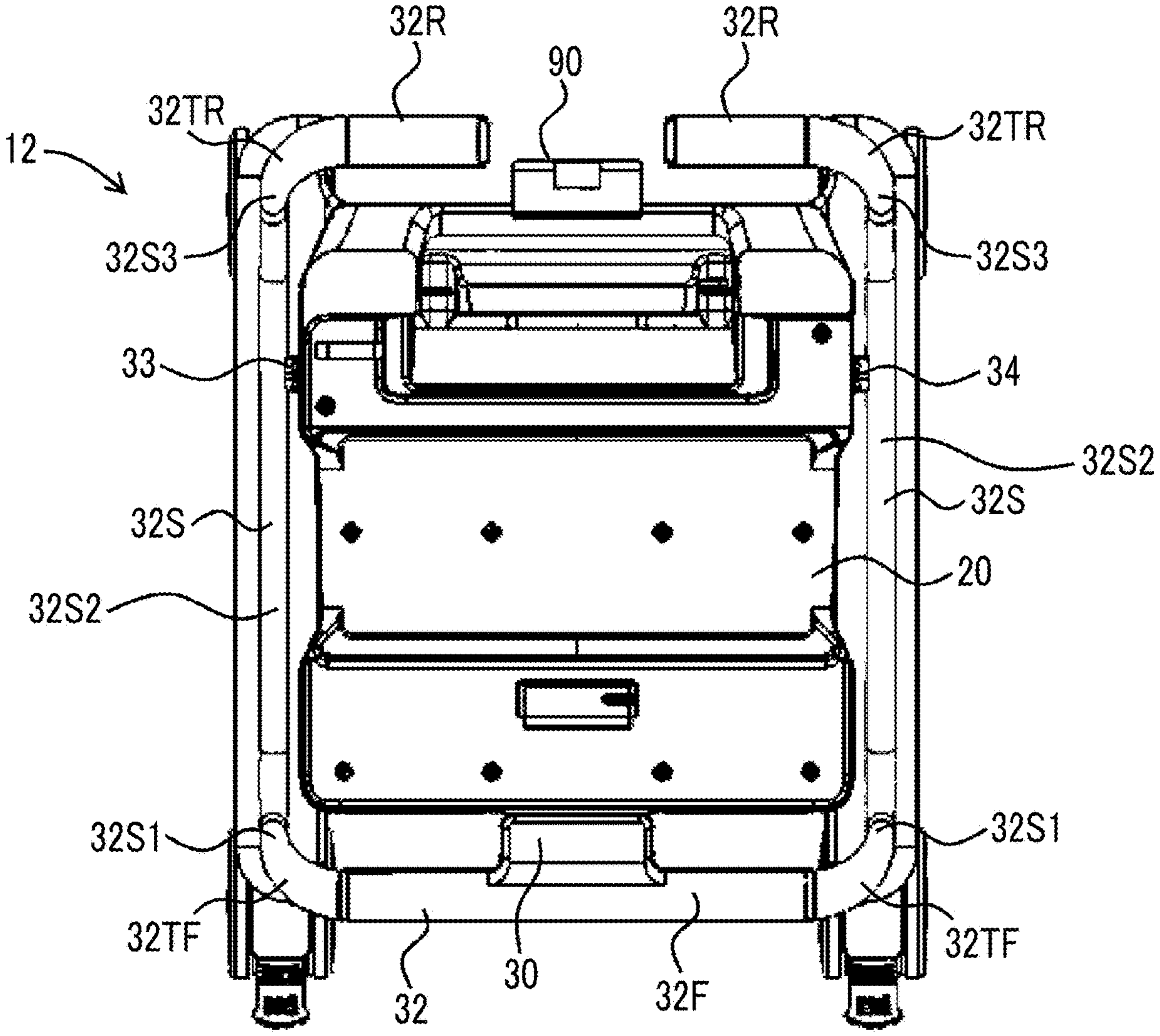
FIG. 14 is a plan view of the cart for an ultrasound diagnostic apparatus.

As shown in FIG. 1, the ultrasound diagnostic unit 10 includes a cart 12 for an ultrasound diagnostic apparatus and a portable ultrasound diagnostic apparatus 100 (hereinafter, will be referred to as the ultrasound diagnostic apparatus 100) placed on a seat 20 of the cart 12. The ultrasound diagnostic apparatus 100 is attachably and detachably mounted onto the seat 20 of the cart 12. FIG. 13 shows a right-side view of the cart 12 after detachment of the ultrasound diagnostic apparatus 100. FIG. 14 shows a plan view of the cart 12 after detachment of the ultrasound diagnostic apparatus 100.

As shown in FIG. 1, the ultrasound diagnostic apparatus 100 is a laptop type ultrasound diagnostic apparatus. The ultrasound diagnostic apparatus 100 includes an operation portion 102 and a display portion 106. The operation portion 102 and the display portion 106 are connected to each other by a hinge. The display portion 106 can be closed toward the operation portion 102 with the hinge as an axis. All of FIGS. 1 to 6 show a state where the display portion 106 is open. The display portion 106 includes a display body 106*a* that includes a display unit, the display unit facing a front side in a state where the display portion 106 is open. Note that FIGS. 9 to 12 show the ultrasound diagnostic unit 10 with the display portion 106 closed.

As shown in FIG. 1, the operation portion 102 includes a touch panel 102*a* and a button portion 102*b*. The button portion 102*b* includes an upper surface 102*ba*, a plurality of buttons, and a trackball 102*bb*. The plurality of buttons are represented by a plurality of small quadrangles, circles, or the like in FIG. 1. The trackball 102*bb* is positioned at the center in a lateral direction, and a user can operate the trackball 102*bb* with a wrist placed on a palm rest 30. In addition, a right-side portion of the operation portion 102 is provided with a connector portion 108*a* (a port) to which a connector of a probe is connected and an air discharge portion 110*a* through which air that has cooled the inside of the ultrasound diagnostic apparatus 100 is discharged. In addition, as shown in FIG. 2, a left-side portion of the operation portion 102 is provided with a connector portion 108*b* (a port) to which a connector of various machines is connected and another air discharge portion 110*b*.

As shown in FIG. 1, the cart 12 includes the seat 20, handles 32, a columnar support 22, a raising and lowering operation portion 50, a support body 23, two leg portions 24, and four casters 26.

The handles 32 are connected to the seat 20. As shown in FIG. 14, the handles 32 include a front handle 32F disposed in front of the seat 20, side handles 32S disposed on right and left sides with respect to the seat 20, and a rear handle 32R disposed behind the seat 20. The handles 32 are connected to each other to surround the seat 20.

As shown in FIG. 14, a center portion of the rear handle 32R in the lateral direction is cut out such that the rear handle 32R is divided in the lateral direction. The rear handle 32R consists of a rear handle element 32R on a left side and a rear handle element 32R on a right side. The rear handle element 32R on the left side extends rightward from an end portion (a transition portion 32TR) of the side handle 32S on the left side. The rear handle element 32R on the right side extends leftward from an end portion (a transition portion 32TR) of the side handle 32S on the right side.

As shown in FIG. 14, the handles 32 are bonded to the seat 20 by the palm rest 30 and two connection portions 33 and 34.

As shown in FIG. 3, the columnar support 22 supports the seat 20 to be raisable and lowerable. The columnar support 22 includes an upper columnar support 22*a* (refer to FIG. 3) to which the seat 20 is connected, a lower columnar support 22*b* disposed below the upper columnar support 22*a*, and a gas spring (not shown) disposed therein. The upper columnar support 22*a* is smaller than the lower columnar support 22*b* in width and thickness in a front-rear direction. The columnar support 22 expands and contracts with the upper columnar support 22*a* inserted into the lower columnar support 22*b*. FIGS. 1 to 6 show the cart 12 in a state after contraction of the columnar support 22, that is, the cart 12 with the seat 20 being at the lowest position or a position close to the lowest position. Note that, in a case where the columnar support 22 is in an expanded state, the upper columnar support 22*a* (refer to FIG. 3) protrudes from the lower columnar support 22*b* to a great degree.

As shown in FIG. 1, the support body 23 is disposed below the lower columnar support 22*b*. The two leg portions 24 are disposed at an interval in the lateral direction and are connected to the support body 23. Each of the two leg portions 24 extends in the front-rear direction and supports the columnar support 22 via the support body 23. At each of the two leg portions 24, the casters 26 are disposed on bottom surfaces of both end portions of the leg portion 24 in the front-rear direction.

As described above, the gas spring is disposed inside the columnar support 22. One end of the gas spring is fixed to the seat 20, and the other end of the gas spring is fixed to the lower columnar support 22*b* or the support body 23 disposed below the lower columnar support 22*b*. The gas spring includes an unlocking pin. The gas spring fixes the seat 20 to the lower columnar support 22*b* in a case where the unlocking pin is in a non-operative state. In addition, in a case where the unlocking pin is in an operative state, the gas spring releases the seat 20 fixed to the lower columnar support 22*b* and biases the seat 20 upward with respect to the lower columnar support 22*b*.

As shown in FIG. 1, the cart 12 includes the raising and lowering operation portion 50 that is disposed below a center of the front handle 32F in the lateral direction. The raising and lowering operation portion 50 is a push-button. In a case where the push-button 50 is pressed, the state of the unlocking pin of the gas spring changes from the non-operative state to the operative state. That is, while the push-button 50 is being pressed, the unlocking pin is in the operative state and the columnar support 22 locked to be unexpandable and uncontractable is unlocked (the seat 20 fixed to the lower columnar support 22*b* is released) so that the seat 20 can be raised and lowered.

The user can lower the seat 20 by pushing the seat 20 downward against the gas spring biasing the seat 20 upward, while pressing the push-button 50. In addition, the user can raise the seat 20 only by pressing the push-button 50 or only by lightly lifting the seat 20 in addition to pressing the push-button 50. According to this embodiment, an operator can adjust the height of the seat 20 by pressing the push-button 50 with a thumb in a state where a hand is placed on, for example, a left portion or a right portion of the front handle 32F.

As shown in FIG. 14, the seat 20 includes the palm rest 30 connected to the front handle 32F. As shown in FIG. 7, the palm rest 30 is disposed in front of the operation portion 102 of the ultrasound diagnostic apparatus 100 while being at a center in the lateral direction. The palm rest 30 is positioned between the front handle 32F and the operation portion 102 of the ultrasound diagnostic apparatus 100. As shown in FIG. 5, the front handle 32F, the palm rest 30, and the upper surface 102*ba* of the operation portion of the ultrasound diagnostic apparatus form a continuous upper surface. Accordingly, an operator can operate the ultrasound diagnostic apparatus 100 with a wrist placed on the front handle 32F and the palm rest 30.

As shown in FIG. 2 (or FIGS. 11 and 12), the seat 20 includes a binding operation portion 90 used to bind the ultrasound diagnostic apparatus 100 to the seat 20, the binding operation portion 90 being provided at a rear surface that faces a region below a gap region between the two rear handle elements 32R. The binding operation portion 90 is a member having a rectangular parallelepiped shape and includes a rotational movement shaft 90*a* provided at a lower portion thereof. The binding operation portion 90 rotationally moves about the rotational movement shaft 90*a* to enter a non-binding state where an upper portion thereof is separated from the rear surface of the seat 20 or a binding state where the upper portion is close to the rear surface of the seat 20.

In a case where the ultrasound diagnostic apparatus 100 is to be mounted to the seat 20, first, the binding operation portion 90 is caused to enter the non-binding state. Then, a rear portion of the ultrasound diagnostic apparatus 100 is placed on the seat 20 in a state where a front portion of the ultrasound diagnostic apparatus 100 is inclined downward and the front portion is aligned with a specified position of a front portion of the seat 20. Thereafter, the state of the binding operation portion 90 is changed to the binding state. Accordingly, the ultrasound diagnostic apparatus 100 is bound to the seat 20. The front portion of the ultrasound diagnostic apparatus 100 is bound to the seat 20 via a structure (for example, a hook and a groove) that is partially hooked on the seat 20. In a case where the state of the binding operation portion 90 is changed from the non-binding state to the binding state, the rear portion of the ultrasound diagnostic apparatus 100 is bound to the seat 20 with a pin protruding from the seat 20 and inserted into a hole in a rear surface of the ultrasound diagnostic apparatus 100.

In this embodiment, since the gap region is present between the two rear handle elements 32R, a user can access the binding operation portion 90 through the gap region and thus it is possible to easily perform attachment and detachment of the ultrasound diagnostic apparatus 100.

As shown in FIG. 1, the front handle 32F extends in the lateral direction. Both end portions of the front handle 32F are bent in a rearward and downward oblique direction to be connected to the side handles 32S. As shown in FIGS. 5 and 6, each of the side handles 32S on the right and left sides includes a front portion 32S1 that is connected to the front handle 32F and that is inclined rearward and downward, a body portion 32S2 that extends rearward from a rear end of the front portion 32S1, and a rear portion 32S3 that extends rearward from a rear end of the body portion 32S2. The body portions 32S2 of the side handles 32S are inclined upward in a direction from a front side to a rear side. The rear portions 32S3 of the side handles 32S are steeply inclined upward in comparison with the body portions 32S2. As shown in FIG. 7, end portions of the rear portions 32S3 of the side handles 32S are bent inward in the lateral direction of the cart 12 and are connected to the rear handle elements 32R. As shown in FIGS. 5 and 6, the rear handle elements 32R are provided at positions higher than the front handle 32F. Regarding the handle 32, as shown in FIG. 7 (or FIG. 14), transition portions 32TF between the front handle 32F and the side handles 32S have rounded shapes and similarly, the transition portions 32TR between the side handles 32S and the rear handle elements 32R have rounded shapes, as seen in a plan view.

The handles 32 have a flat oval cross-sectional outer shape over the entire periphery. FIG. 7 shows an A-A cross section as a cross section of the front handle 32F, a B-B cross section as a cross section of the side handles 32S, and a C-C cross section as a cross section of the rear handle 32R. The front handle 32F and the rear handle 32R are disposed such that flat surfaces thereof face a vertical direction. The two side handles 32S are disposed such that the flat surfaces thereof face the lateral direction.

Figure 8:
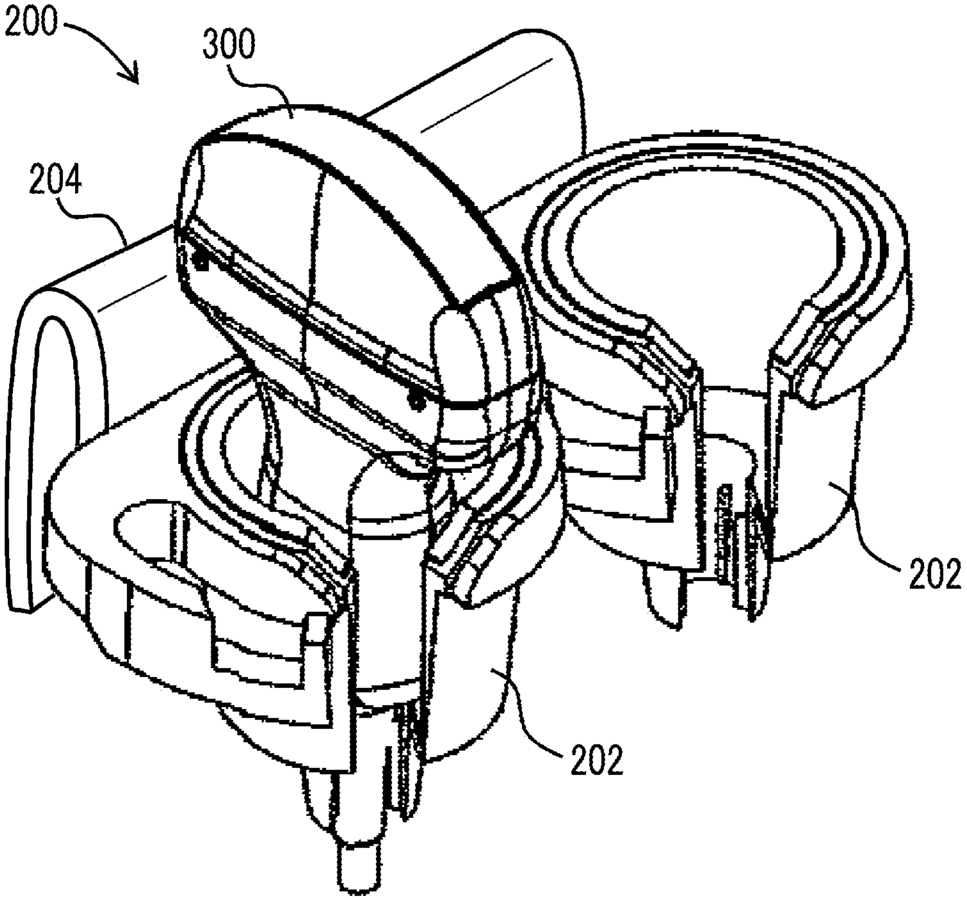
FIG. 8 is a perspective view showing an example of a probe holder.
Figure 9:
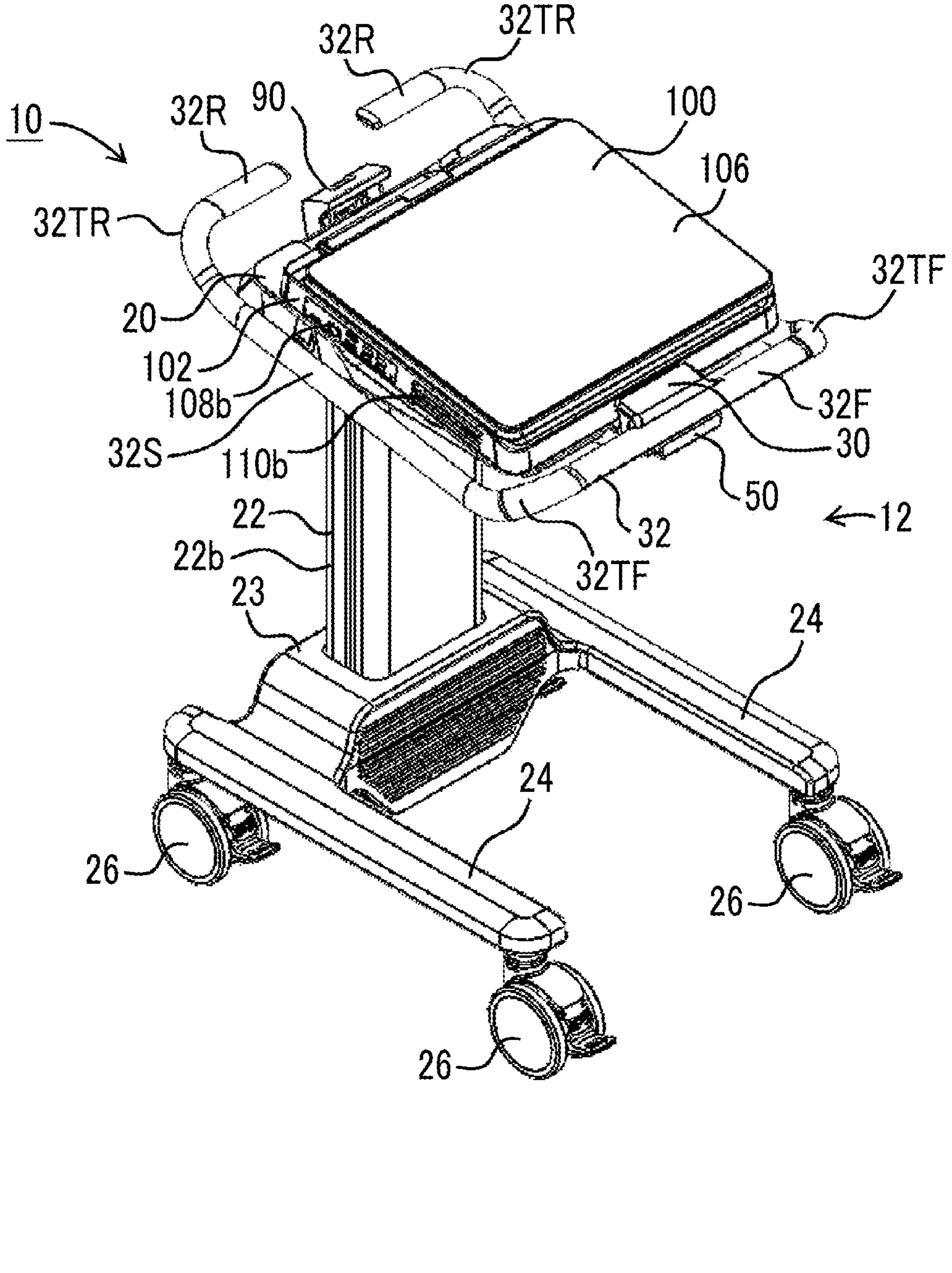
FIG. 9 is a perspective view showing the front surface and the left side surface of the ultrasound diagnostic unit and shows a state where a display portion of a portable ultrasound diagnostic apparatus is closed.
Figure 10:
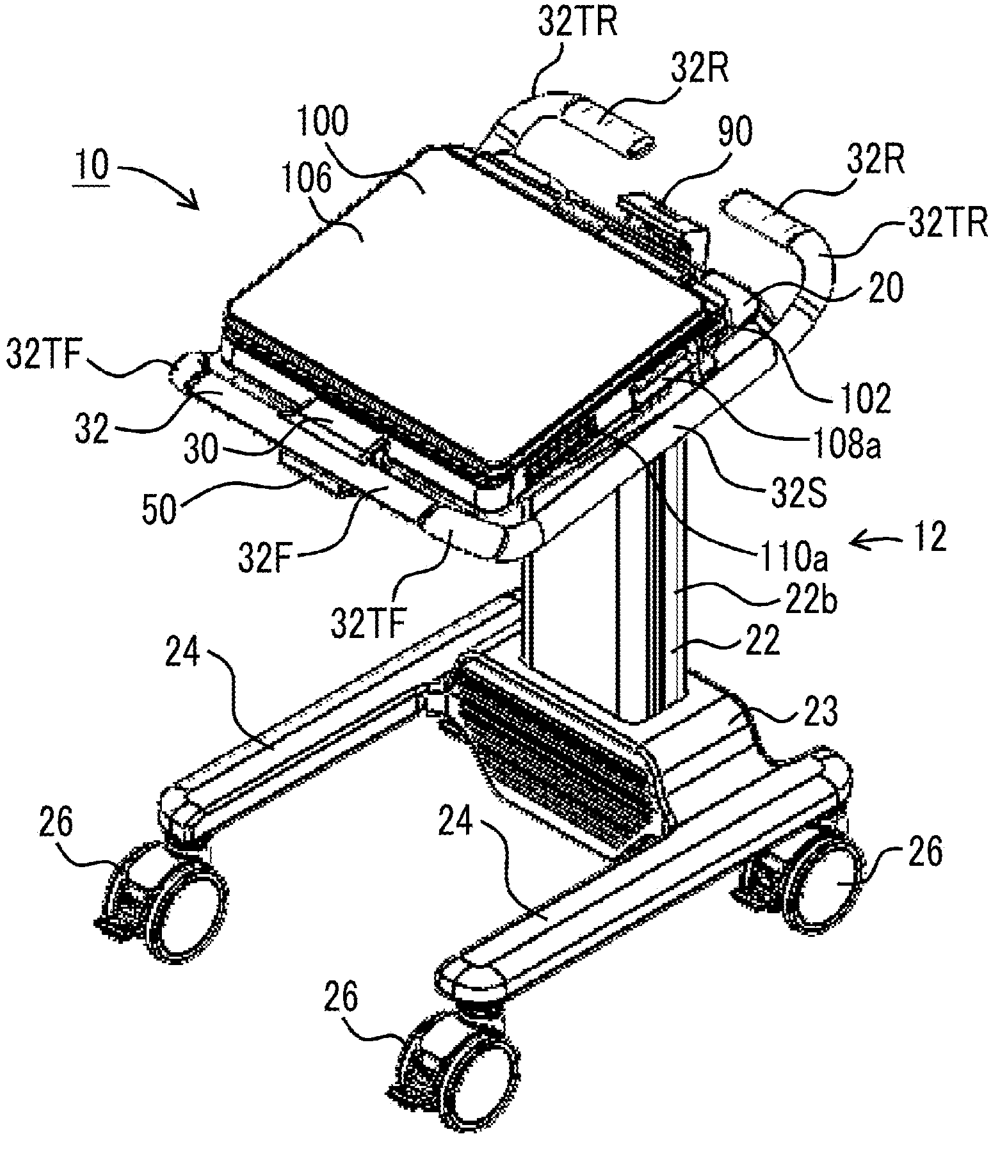
FIG. 10 is a perspective view showing the front surface and the right side surface of the ultrasound diagnostic unit and shows a state where the display portion of the portable ultrasound diagnostic apparatus is closed.
Figure 11:
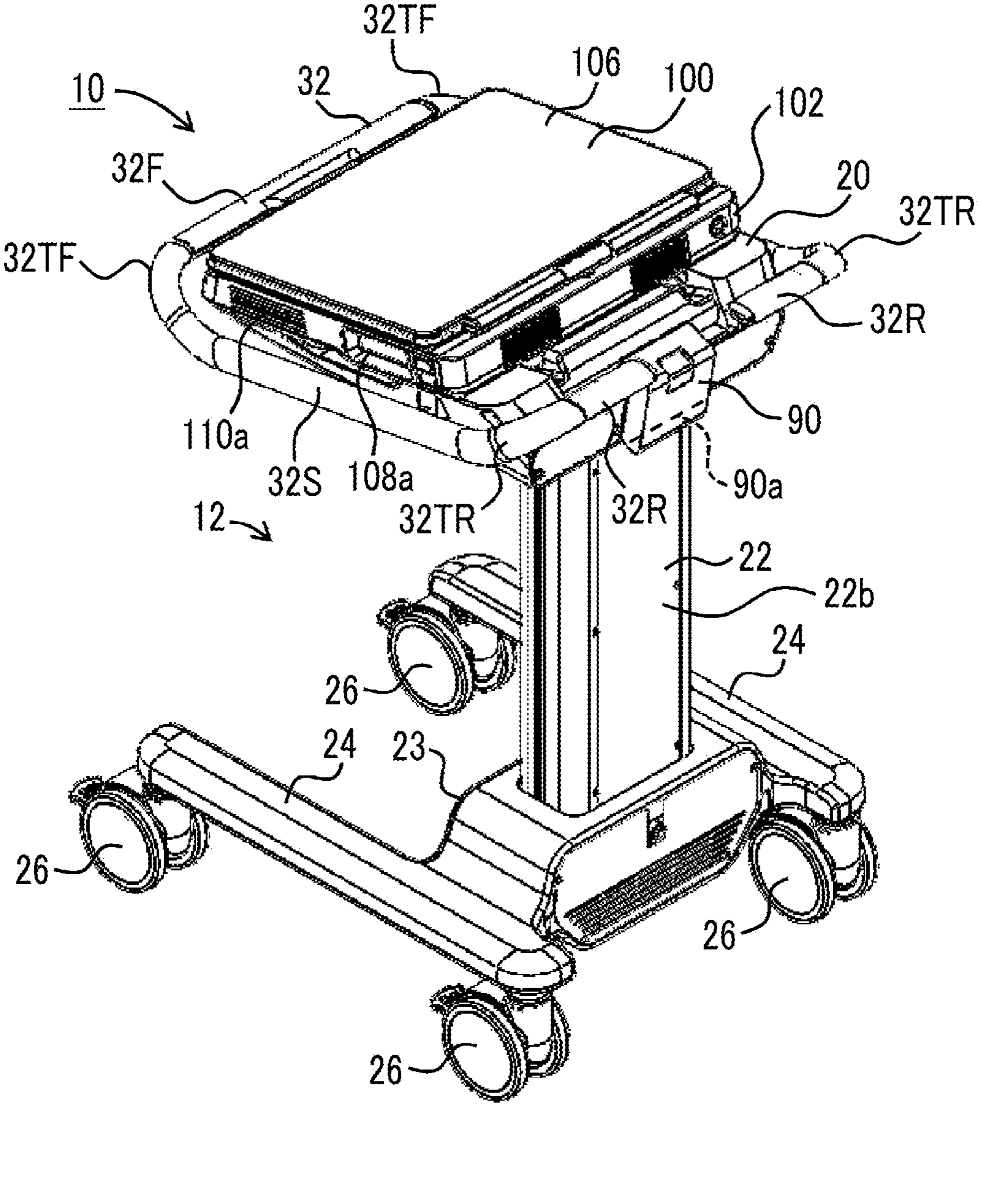
FIG. 11 is a perspective view showing the rear surface and the right side surface of the ultrasound diagnostic unit and shows a state where the display portion of the portable ultrasound diagnostic apparatus is closed.
Figure 12:
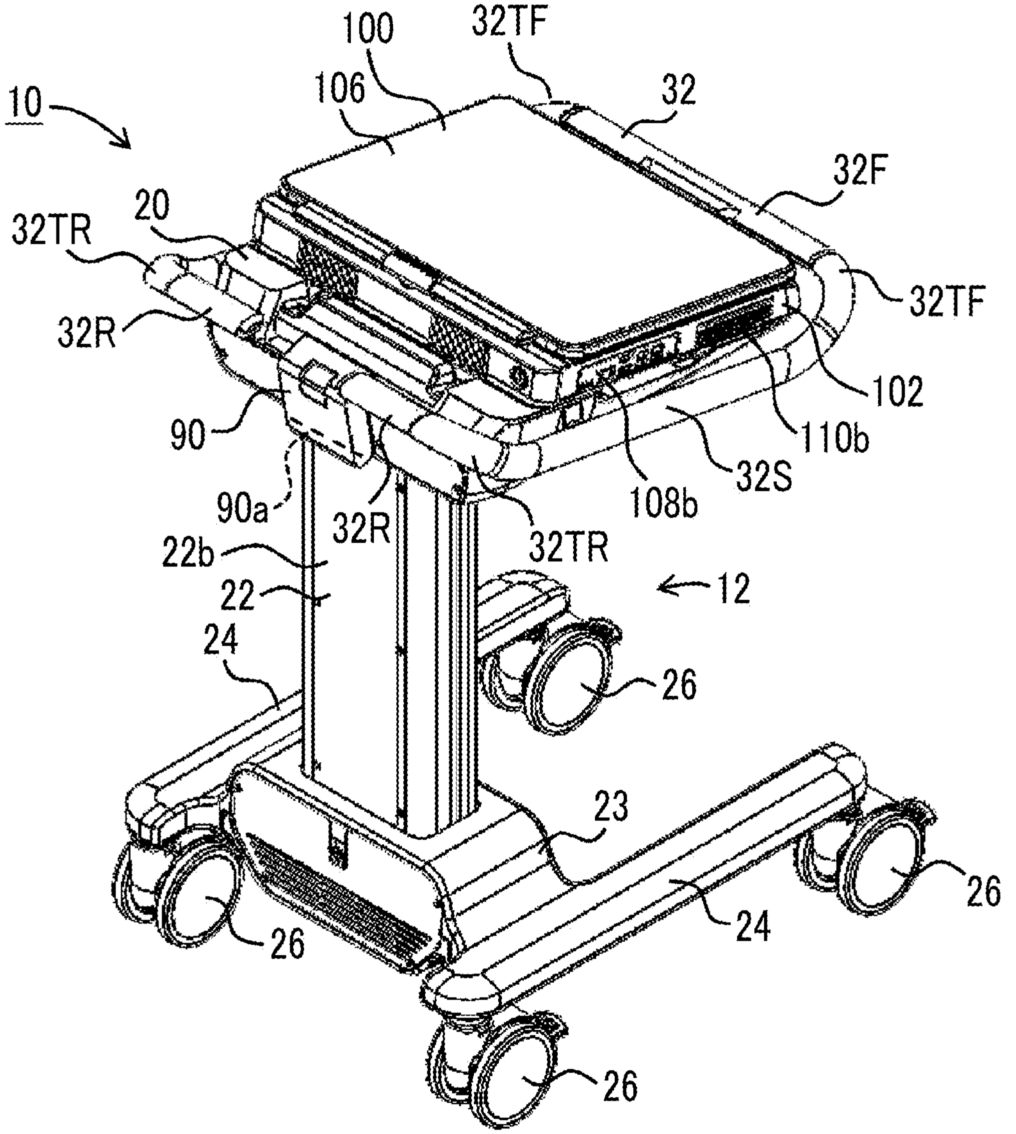
FIG. 12 is a perspective view showing the rear surface and the left side surface of the ultrasound diagnostic unit and shows a state where the display portion of the portable ultrasound diagnostic apparatus is closed.

For example, a probe holder, a holder that holds a jelly container, a holder that holds a tray, or the like is attached to one or both of the two side handles 32S. In FIGS. 1, 6, and 7, an example of a position where a probe holder 200 is attached is represented by virtual lines. FIG. 8 shows an example of the probe holder 200. The probe holder 200 includes one or a plurality of holder elements 202 and a hook 204. A probe head 300 is inserted into and supported by the holder elements 202. The probe holder 200 is attached to the side handle 32S with the hook 204 of the probe holder 200 hooked on the side handle 32S.

According to the embodiment described above, since the handles 32 are provided around the seat 20, a user can access the handles 32 and move the ultrasound diagnostic unit 10 regardless of the user's position with respect to the ultrasound diagnostic unit 10. For example, the user can finely adjust the position of the ultrasound diagnostic unit 10 or can revolve the ultrasound diagnostic unit 10 while gripping the front handle 32F or the rear handle 32R with one hand and gripping the side handle 32S with the other hand. For example, the user can grip the rear handle 32R to transport the ultrasound diagnostic unit 10.

In addition, according to the embodiment described above, since the handles 32 are connected to each other and corner portions (the transition portions 32TF and 32TR) of the handles 32 have the rounded shapes, a white coat or the like is restrained from being caught on the handles 32.

In addition, according to the embodiment described above, since the body portions 32S2 of the two side handles 32S are provided at relatively low positions as shown in FIG. 5, FIG. 6, and the like, side portions of the ultrasound diagnostic apparatus 100 can be made open. Note that the expression "being provided at relatively low positions" means that the body portions 32S2 of the two side handles 32S are provided at positions lower than the upper surface of the operation portion 102 of the ultrasound diagnostic apparatus 100. That is, the body portions 32S2 of the two side handles 32S extend to be parallel or substantially parallel to the upper surface of the operation portion 102 of the ultrasound diagnostic apparatus 100. In addition, the body portions 32S2 of the two side handles 32S are provided at positions lower than the upper surface of the operation portion 102 of the ultrasound diagnostic apparatus 100 in a direction (an approximately vertical direction) orthogonal to a direction in which the body portions 32S2 of the two side handles 32S extend. Therefore, the side portions of the operation portion 102 of the ultrasound diagnostic apparatus 100 can be made open. It becomes easy to access the connector portions 108*a* and 108*b* of the ultrasound diagnostic apparatus 100 and the air discharge portions 110*a* and 110*b* are restrained from being blocked.

In addition, according to the embodiment described above, the rear handle 32R is provided at a position higher than the front handle 32F. Therefore, in a case where the front handle 32F is at a relatively low position in consideration of a case where an operator operates the ultrasound diagnostic apparatus 100 in a seated position, the rear handle 32R is at a high position. Accordingly, for example, in a case where a user transports the ultrasound diagnostic unit 10 while holding the rear handle 32R, the user can easily perform the transportation.

In addition, according to the embodiment described above, as shown in FIGS. 5 and 6, the body portions 32S2 of the two side handles 32S are inclined upward in the direction from the front side to the rear side. Therefore, in a case where a holder such as the probe holder 200 is attached to the body portion 32S2 of the side handle 32S, an object (for example, the probe head 300) held by the holder faces a diagonally front side. Therefore, an operator can easily access the object held by the holder.

In addition, according to the embodiment described above, the handles 32 have a flat oval cross-sectional outer shape over the entire periphery. Therefore, the rigidity of the handles 32 can be increased. In addition, since the front handle 32F and the rear handle 32R are disposed such that the flat surfaces thereof face the vertical direction, a user can move the ultrasound diagnostic unit 10 while holding the front handle 32F or the rear handle 32R with a hand being in close contact with an upper flat surface of the handle. In addition, since the two side handles 32S are disposed such that the flat surfaces thereof face the lateral direction, the amount of protrusion of the side handles 32S in the lateral direction can be suppressed in comparison with a case where the side handles 32S are disposed such that the flat surfaces thereof face the vertical direction.

What is claimed is:

1. An ultrasound diagnostic unit comprising:
a portable ultrasound diagnostic apparatus;
a seat on which the portable ultrasound diagnostic apparatus is placed;
handles that are connected to the seat;
a columnar support that supports the seat;
a plurality of leg portions that support the columnar support; and
casters that are disposed at the leg portions,
wherein the handles include a front handle disposed in front of the seat, side handles disposed on right and left sides with respect to the seat, and a rear handle disposed behind the seat,
the handles are connected to each other to surround the seat, and
each of two side handles includes a front portion that is connected to the front handle and that is inclined rearward and downward and a body portion that extends rearward from a rear end of the front portion;
wherein the seat includes a palm rest that is disposed in front of an operation portion of the portable ultrasound diagnostic apparatus while being at a center in a lateral direction,
the palm rest is positioned between the front handle and the operation portion of the portable ultrasound diagnostic apparatus, and
the front handle, the palm rest, and the operation portion of the portable ultrasound diagnostic apparatus form a continuous upper surface;
wherein a center portion of the rear handle in a lateral direction is cut out such that the rear handle is divided in the lateral direction,
the rear handle consists of a rear handle element on the left side and a rear handle
element on the right side, and
the seat includes an operation portion used to bind the portable ultrasound diagnostic apparatus to the seat, the operation portion being provided at a rear surface that faces at least one of a gap region between two rear handle elements or a region below the gap region.

2. The ultrasound diagnostic unit according to claim 1, wherein the rear handle is provided at a position higher than the front handle.

3. The ultrasound diagnostic unit according to claim 2, wherein the rear handle is provided at a position higher than the front handle.

4. The ultrasound diagnostic unit according to claim 2, wherein the body portion of each of the two side handles is inclined upward in a direction from a front side to a rear side.

5. The ultrasound diagnostic unit according to claim 3, wherein the body portion of each of the two side handles is inclined upward in a direction from a front side to a rear side.

6. The ultrasound diagnostic unit according to claim 1, wherein a cross-sectional outer shape of the handles is a flat oval shape, the front handle and the rear handle are disposed such that flat surfaces of the front handle and the rear handle face a vertical direction, and the two side handles are disposed such that flat surfaces of the side handles face a lateral direction.

7. The ultrasound diagnostic unit according to claim 2, wherein a cross-sectional outer shape of the handles is a flat oval shape, the front handle and the rear handle are disposed such that flat surfaces of the front handle and the rear handle face a vertical direction, and the two side handles are disposed such that flat surfaces of the side handles face a lateral direction.

8. The ultrasound diagnostic unit according to claim 1, wherein a center portion of the rear handle in a lateral direction is cut out such that the rear handle is divided in the lateral direction, the rear handle consists of a rear handle element on the left side and a rear handle element on the right side, and the seat includes an operation portion used to bind the portable ultrasound diagnostic apparatus to the seat, the operation portion being provided at a rear surface that faces at least one of a gap region between two rear handle elements or a region below the gap region.

9. The ultrasound diagnostic unit according to claim 1, wherein the columnar support supports the seat to be raisable and lowerable, the ultrasound diagnostic unit further comprises a push-button used to raise or lower the seat, the push-button is disposed below a center of the front handle in a lateral direction, and the seat locked to be unraisable and unlowerable is unlocked in a case where the push-button is pressed.

10. The ultrasound diagnostic unit according to claim 2, wherein the columnar support supports the seat to be raisable and lowerable, the ultrasound diagnostic unit further comprises a push-button used to raise or lower the seat, the push-button is disposed below a center of the front handle in a lateral direction, and the seat locked to be unraisable and unlowerable is unlocked in a case where the push-button is pressed.

11. A cart for an ultrasound diagnostic apparatus, the cart comprising:

a seat on which a portable ultrasound diagnostic apparatus is placed;

handles that are connected to the seat;

a columnar support that supports the seat;

a plurality of leg portions that support the columnar support; and casters that are disposed at the leg portions, wherein the handles include a front handle disposed in front of the seat, side handles disposed on right and left sides with respect to the seat, and a rear handle disposed behind the seat, the handles are connected to each other to surround the seat, and each of two side handles includes a front portion that is connected to the front handle and that is inclined rearward and downward and a body portion that extends rearward from a rear end of the front portion;

wherein the seat includes a palm rest that is disposed in front of an operation portion of the portable ultrasound diagnostic apparatus while being at a center in a lateral direction, the palm rest is positioned between the front handle and the operation portion of the portable ultrasound diagnostic apparatus, and the front handle, the palm rest, and the operation portion of the portable ultrasound diagnostic apparatus form a continuous upper surface;

wherein a center portion of the rear handle in a lateral direction is cut out such that the rear handle is divided in the lateral direction, the rear handle consists of a rear handle element on the left side and a rear handle element on the right side, and the seat includes an operation portion used to bind the portable ultrasound diagnostic apparatus to the seat, the operation portion being provided at a rear surface that faces at least one of a gap region between two rear handle elements or a region below the gap region.

12. The cart for an ultrasound diagnostic apparatus according to claim 11, wherein the rear handle is provided at a position higher than the front handle.

* * * * *